(12) United States Patent
Totani et al.

(10) Patent No.: US 12,187,998 B2
(45) Date of Patent: Jan. 7, 2025

(54) CULTURE CONTAINER, METHOD FOR MANUFACTURING CULTURE CONTAINER, LAMINATED STRUCTURE, AND METHOD FOR MANUFACTURING LAMINATED STRUCTURE

(71) Applicant: TOYO SEIKAN GROUP HOLDINGS, LTD., Tokyo (JP)

(72) Inventors: Takahiko Totani, Kanagawa (JP); Satoshi Tanaka, Kanagawa (JP); Yosuke Matsuoka, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 612 days.

(21) Appl. No.: 16/743,911

(22) Filed: Jan. 15, 2020

(65) Prior Publication Data

US 2020/0148992 A1    May 14, 2020

Related U.S. Application Data

(63) Continuation of application No. PCT/JP2018/025017, filed on Jul. 2, 2018.

(30) Foreign Application Priority Data

Jul. 22, 2017  (JP) .................. 2017-142318
Oct. 17, 2017  (JP) .................. 2017-201441

(51) Int. Cl.
    *C12M 1/00*        (2006.01)
    *C12M 1/12*        (2006.01)
(52) U.S. Cl.
    CPC ............ *C12M 23/26* (2013.01); *C12M 23/20* (2013.01); *C12M 25/02* (2013.01)

(58) Field of Classification Search
    CPC ....... C12M 23/26; C12M 23/20; C12M 25/02
    See application file for complete search history.

(56) References Cited

U.S. PATENT DOCUMENTS

| 4,945,203 A | 7/1990 | Soodak et al. |
| 7,919,305 B2 | 4/2011 | Miyake et al. |
| (Continued) | | |

FOREIGN PATENT DOCUMENTS

| EP | 0356785 A1 | 3/1990 |
| EP | 2628789 A1 | 8/2013 |
| (Continued) | | |

OTHER PUBLICATIONS

Translation of JP-3728686 obtained Apr. 2024 (Year: 2024).*
(Continued)

*Primary Examiner* — William H. Beisner
*Assistant Examiner* — Danielle B Henkel
(74) *Attorney, Agent, or Firm* — Osha Bergman Watanabe & Burton LLP

(57) ABSTRACT

A culture container made of a flexible packaging material where the culture container includes a first side surface portion and a second side surface portion that are mutually opposed. The culture container also includes at least an inner surface side of the first side surface portion which has a surface treatment such that, when a contact angle hysteresis is defined as an advance contact angle—a retreat contact angle at a time when water slips, a contact angle hysteresis of a surface on the inner surface side of the first side surface portion becomes larger than a contact angle hysteresis of a surface on an inner surface side of the second side surface portion. The culture container further includes a membrane made of a cell adhesion inhibitor that is formed on the inner surface side of the first side surface portion.

3 Claims, 15 Drawing Sheets

[Fig. 2A]

(56) References Cited

U.S. PATENT DOCUMENTS

| | | | |
|---|---|---|---|
| 8,486,692 B2* | 7/2013 | Simon | C12M 23/24 |
| | | | 435/297.5 |
| 2010/0047845 A1* | 2/2010 | Woodside | C08J 7/0427 |
| | | | 435/325 |
| 2013/0230914 A1* | 9/2013 | Totani | C12M 25/14 |
| | | | 264/447 |
| 2014/0227784 A1* | 8/2014 | Ejiri | C12M 23/20 |
| | | | 435/395 |
| 2014/0326391 A1 | 11/2014 | Kuroda et al. | |

FOREIGN PATENT DOCUMENTS

| | | | |
|---|---|---|---|
| JP | H3-160984 A | | 7/1991 |
| JP | H06-098756 A | | 4/1994 |
| JP | H08131153 A | | 5/1996 |
| JP | 3728686 B2 | * | 12/2005 |
| JP | 2009027945 A | | 2/2009 |
| JP | 2012175983 A | | 9/2012 |
| JP | 2013-70636 A | | 4/2013 |
| WO | 2012/036011 A1 | | 3/2012 |
| WO | 2014083539 A1 | | 6/2014 |

OTHER PUBLICATIONS

International Search Report issued in corresponding International Application No. PCT/JP2018/025017 dated Aug. 21, 2018, with translation (5 pages).

* cited by examiner

[Fig. 1A]
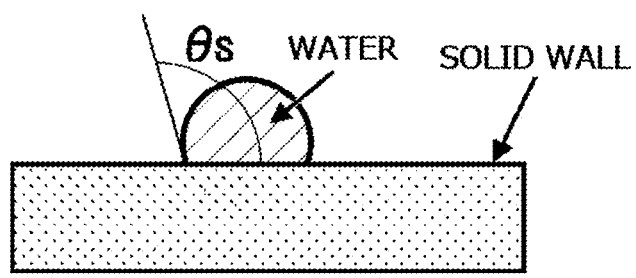

[Fig. 1B]
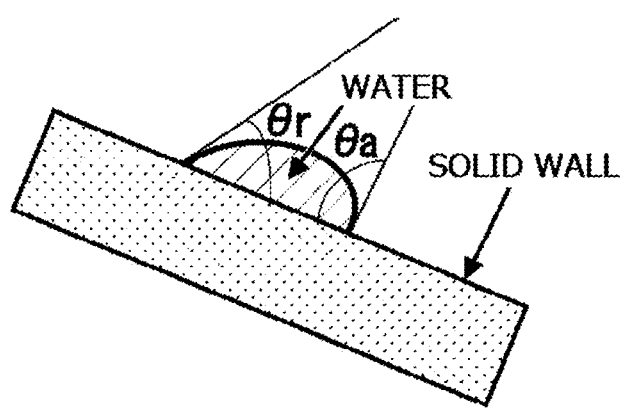

[Fig. 2A]
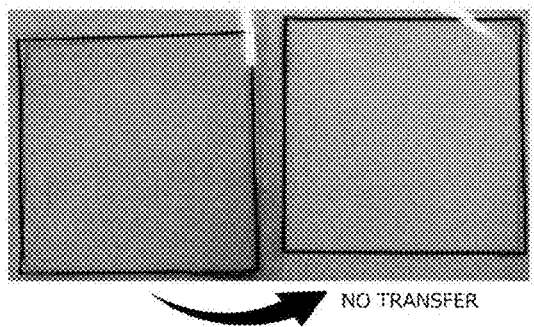
[Fig. 2B]
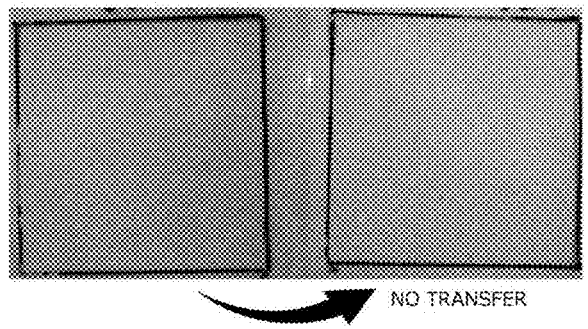
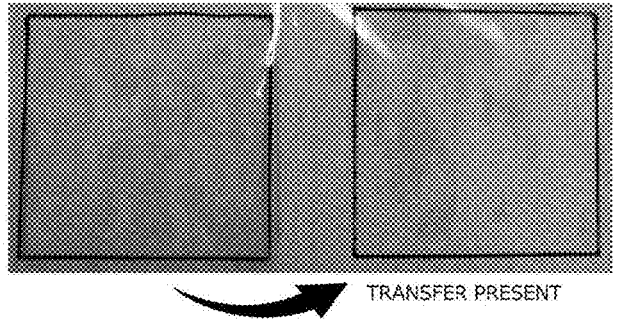
[Fig. 2C]

[Fig. 3A]
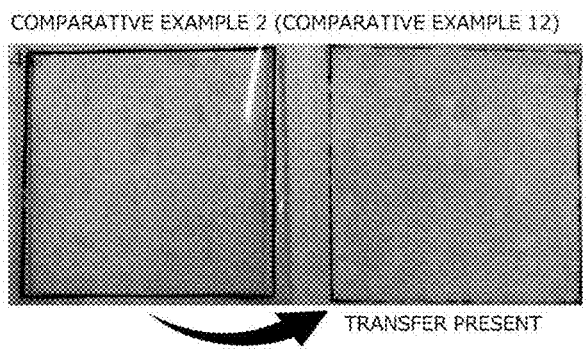
[Fig. 3B]
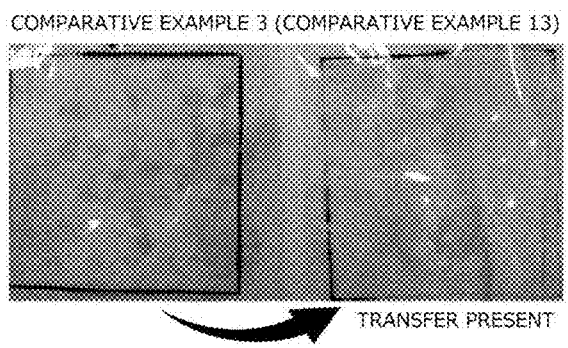
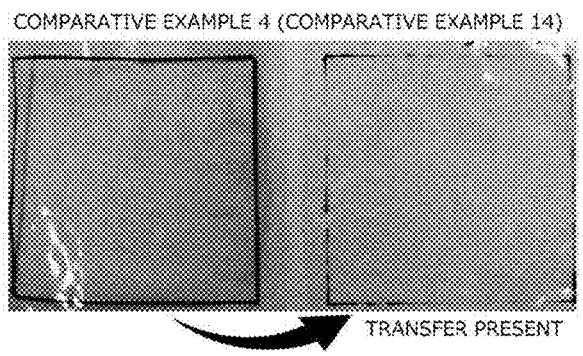
[Fig. 3C]

[Fig. 4A]
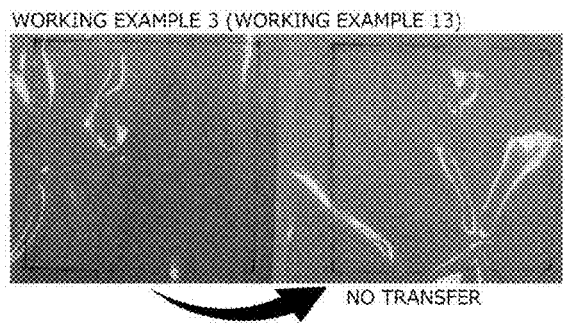
[Fig. 4B]
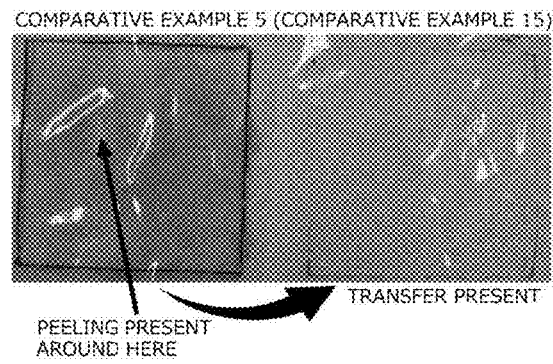

[Fig. 5A]
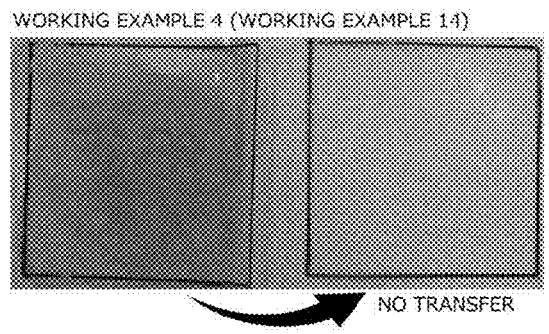
WORKING EXAMPLE 4 (WORKING EXAMPLE 14)
NO TRANSFER
[Fig. 5B]
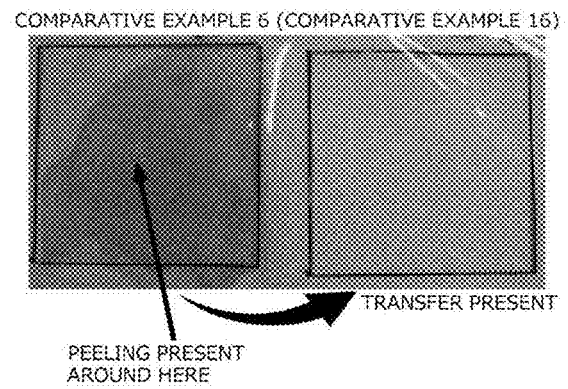
COMPARATIVE EXAMPLE 6 (COMPARATIVE EXAMPLE 16)
PEELING PRESENT AROUND HERE
TRANSFER PRESENT

[Fig. 6A]
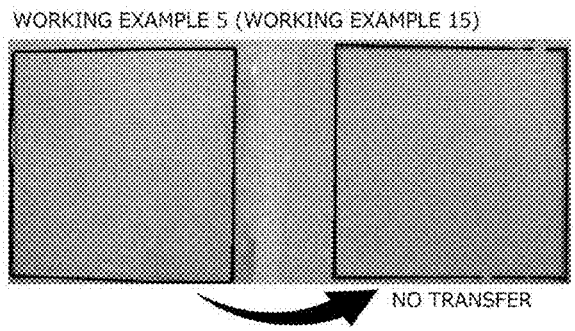
[Fig. 6B]
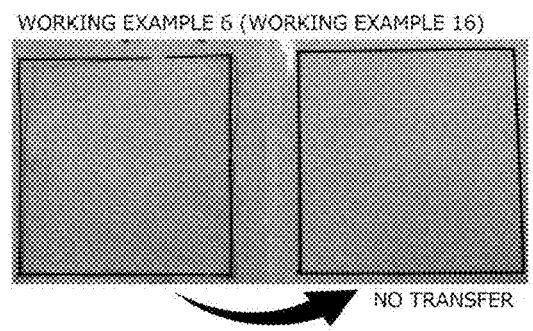
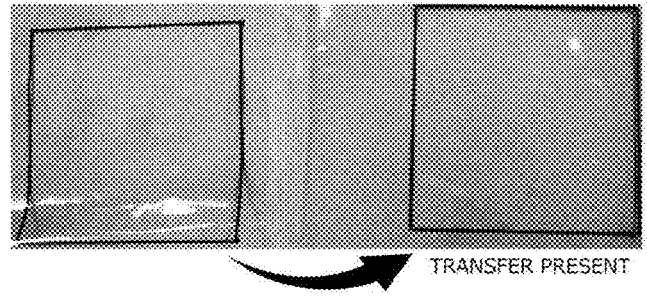
[Fig. 6C]

[Fig. 7]
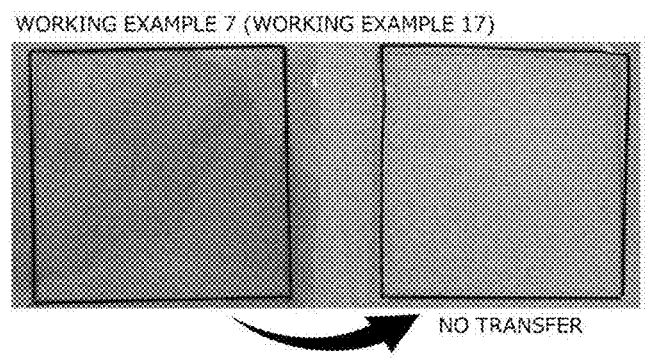

[Fig. 8]
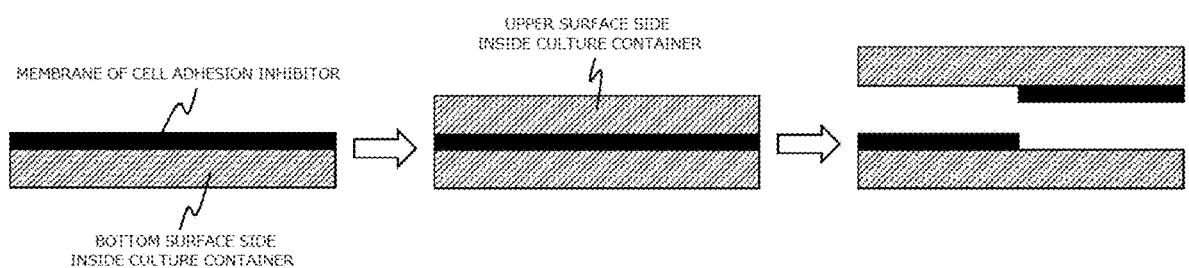

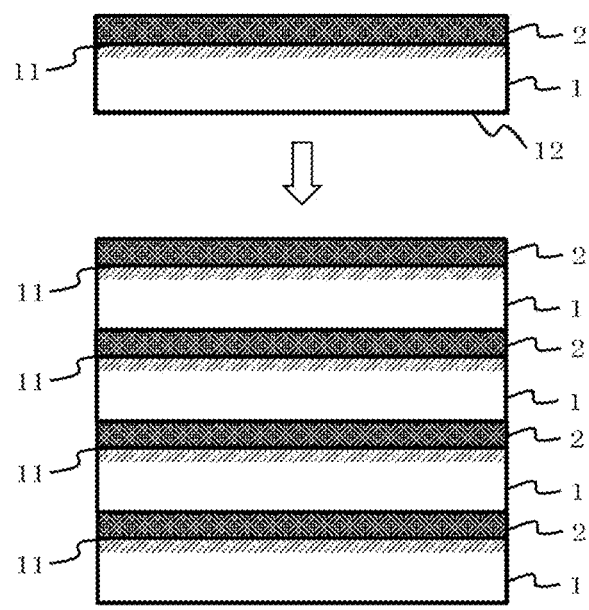
[Fig. 9]

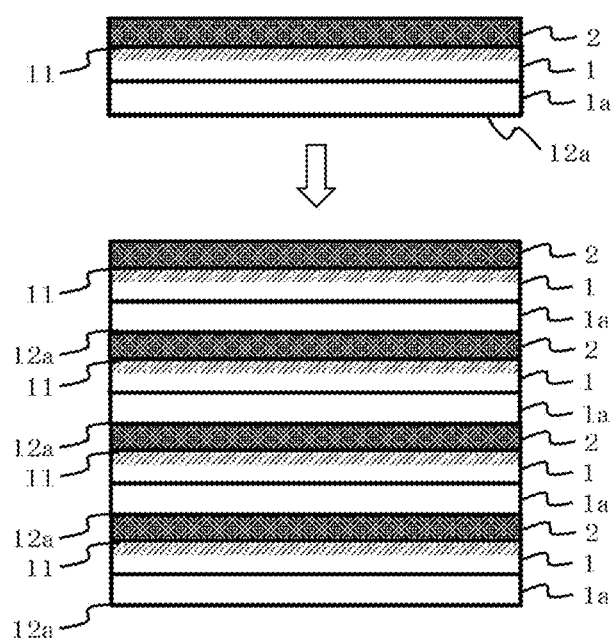
[Fig. 10]

[Fig. 11]
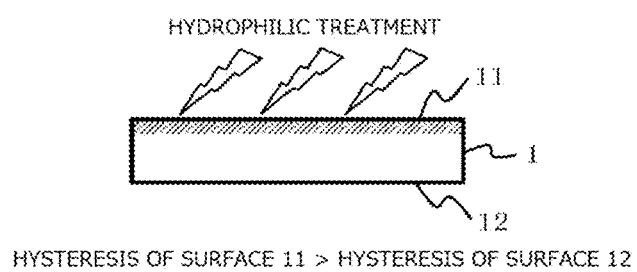
HYSTERESIS OF SURFACE 11 > HYSTERESIS OF SURFACE 12
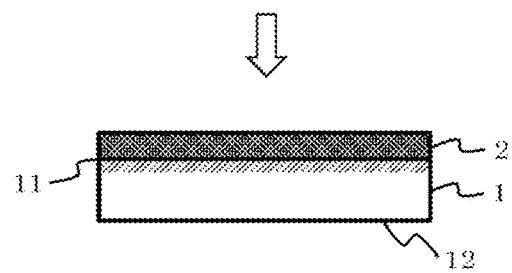

[Fig. 12]
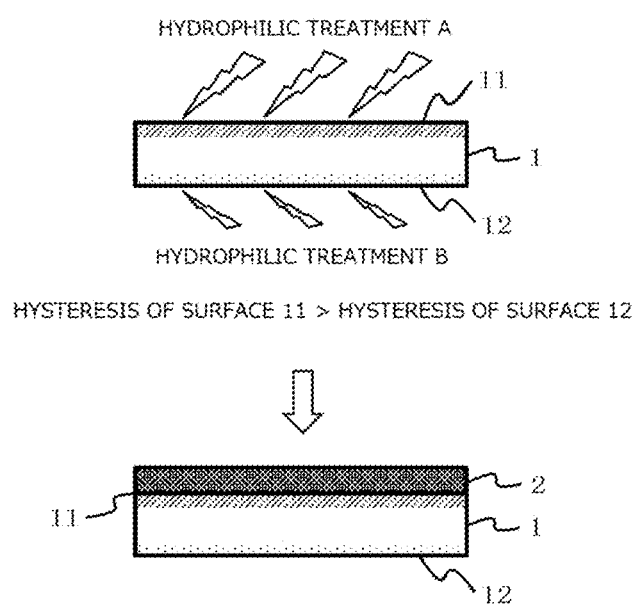

[Fig. 13]
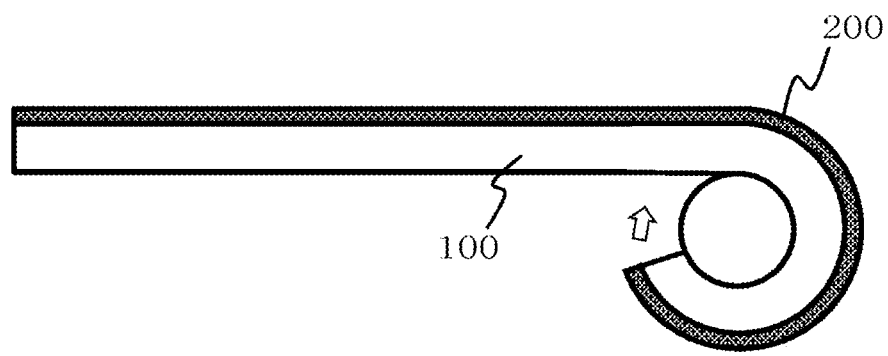

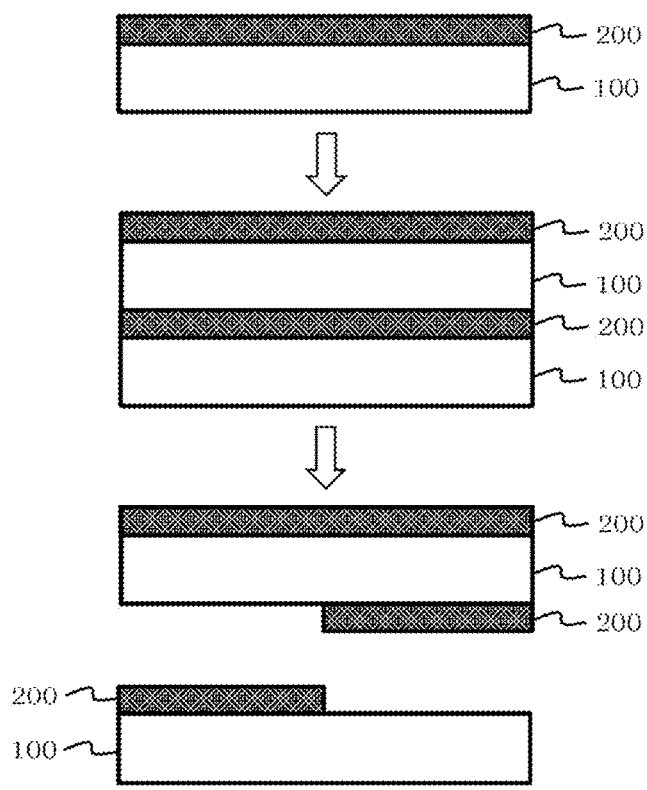
[Fig. 14]

CULTURE CONTAINER, METHOD FOR MANUFACTURING CULTURE CONTAINER, LAMINATED STRUCTURE, AND METHOD FOR MANUFACTURING LAMINATED STRUCTURE

TECHNICAL FIELD

One or more embodiments of the present invention relate to a cell culture technique, in particular, relates to a culture container used for a sphere culture.

One or more embodiments of the present invention also relate to a laminated structure for manufacturing a cell culture container and the like, and a method for manufacturing the same.

BACKGROUND

Recently, it has been demanded to efficiently culture a large number of cells, tissues, microorganisms, and the like under an artificial environment in a medicinal product production and a field, such as gene therapy, regeneration medicine, and immunotherapy.

In such a situation, a large number of cells are automatically cultured in a closed system by filling the cells and a culture fluid in a culture container.

Recently, there has been used a method that, without adhering adherent cells, such as iPS cells, to a culture container, cultures the cells by floating the cells in the culture container to cause the cells to form a sphere (aggregate), thereby improving culture efficiency of the cells. In this case, a bottom surface inside the culture container usually needs to be applied (coated) with a cell adhesion inhibitor so as not to cause the cells to adhere.

Here, Patent Document 1 proposes a culture base material having dents the inner surfaces of which are applied with a cell adhesion inhibitor in relation to a culture method that forms a sphere. This culture base material is a rigid one, with which the sphere is considered to be appropriately formable by applying the cell adhesion inhibitor on the inner surface.

A film and a sheet (hereinafter, simply referred to as a film in some cases) used in manufacturing the cell culture container had to be stored until the cell culture container is manufactured after the cell adhesion inhibitor was applied on its surface.

Patent Document 1: WO 2012/036011 pamphlet
Patent Document 2: JP-A-2013-70636

When a large number of cells are efficiently cultured, it may be preferred to automatically culture the cells in a closed system using a culture container made of a flexible packaging material, which can relatively easily manufacture a large-volumed culture container.

However, such a culture container made of the flexible packaging material generally has a bag shape. Therefore, there has been a problem that, when a cell adhesion inhibitor is applied on a bottom surface in the culture container, a contact between the bottom surface and a top surface inside the culture container causes a membrane of the cell adhesion inhibitor applied on the bottom surface to be transferred onto the top surface as illustrated in FIG. 8, and thus the membrane of the cell adhesion inhibitor comes off of the bottom surface.

That is, the membrane of the cell adhesion inhibitor thus coming off of the bottom surface causes the cells to adhere on the bottom surface portion from which the cell adhesion inhibitor has come off. Therefore, the cells can no longer appropriately form a sphere, thereby causing a problem of hindering the sphere culture.

Therefore, through their extensive research, the inventors have completed one or more embodiments of the present invention by successfully manufacturing a culture container with which the membrane of the cell adhesion inhibitor is not transferred from the bottom surface onto the top surface by processing a base material of the bottom surface and the top surface inside the culture container with a specific condition.

That is, a surface treatment is performed on a surface side on which at least the cell adhesion inhibitor is applied such that a contact angle hysteresis of the surface on which the cell adhesion inhibitor is applied in the culture container becomes larger than a contact angle hysteresis of an opposite surface, and the membrane of the cell adhesion inhibitor is formed on the surface. Thus, it is possible to avoid the membrane of the cell adhesion inhibitor coming off to be transferred onto the opposite surface side.

The film on which the cell adhesion inhibitor is applied is rolled up into a roll shape and stored in some cases, and there has been a problem that the cell adhesion inhibitor comes off of the film when the film is spread into a planar shape when in use.

Specifically, as illustrated in FIG. 13 and FIG. 14, when the film is rolled up into the roll shape, a coating layer 200 formed by applying a cell adhesion inhibitor on a culture base material 100 is brought into a close contact with a surface on the opposite side of the coating layer 200 on the culture base material 100.

There has been a problem that, when the film is returned into the planar shape, the coating layer 200 comes off of the surface of the culture base material 100 to be transferred onto the surface on the opposite side of the culture base material 100.

Therefore, through their extensive research, the inventors have completed one or more embodiments of the present invention by successfully manufacturing a laminated structure that does not cause a transfer of the coating layer by treating a hydrophilicity of a first surface of a flexible film or sheet shaped culture base material to be higher than a hydrophilicity of a second surface on an opposite side of the first surface, and forming a laminated structure by forming a coating layer on the first surface and rolling up the culture base material into the roll shape.

Here, Embodiment 1 in Patent Document 2 discloses performing a cell adhesion reduction treatment by performing a plasma treatment on a surface of a culture base material.

However, this culture base material does not have a flexibility and do not ensure forming the laminated structure without causing the transfer of the coating layer by considering a hydrophilicity on both surfaces of the culture base material.

One or more embodiments of the present invention has been made in consideration of such circumstances, and it is an object of one or more embodiments of the present invention to provide a culture container that ensures avoiding a cell adhesion inhibitor applied on one inner surface coming off to be transferred on another inner surface caused by the inner surfaces of the culture container are brought into contact in manufacturing the culture container made of a flexible packaging material for a sphere culture, and a method for manufacturing the culture container.

SUMMARY

One or more embodiments of the present invention has been made in consideration of such circumstances, and it is an object of one or more embodiments of the present invention to provide a laminated structure that does not cause a transfer of the coating layer formed on a surface of a culture base material in the laminated structure formed by rolling up the culture base material into a roll shape, and a method for manufacturing the same.

In order to achieve the above-described object, a culture container of one or more embodiments of the present invention is a culture container made of a flexible packaging material. The culture container includes a first side surface portion and a second side surface portion that are mutually opposed. At least an inner surface side of the first side surface portion has a surface treatment such that, when a contact angle hysteresis is defined as an advance contact angle—a retreat contact angle at a time when water slips, a contact angle hysteresis of a surface on the inner surface side of the first side surface portion becomes larger than a contact angle hysteresis of a surface on an inner surface side of the second side surface portion. A membrane made of a cell adhesion inhibitor is formed on the inner surface side of the first side surface portion.

A method for manufacturing a culture container of one or more embodiments of the the present invention is a method for manufacturing a culture container for a sphere culture. The method includes: performing a hydrophilic treatment on a part of a film or a sheet made of a polyolefin; forming the culture container that has a first side surface portion and a second side surface portion, the first side surface portion having a surface on which the hydrophilic treatment of the film or the sheet is performed on an inner surface side, the second side surface portion opposing the first side surface portion, the culture container having a contact angle hysteresis of a surface on the inner surface side of the first side surface portion larger than a contact angle hysteresis of a surface on an inner surface side of the second side surface portion when the contact angle hysteresis is defined as an advance contact angle—a retreat contact angle at a time when water slips; and applying a cell adhesion inhibitor on the inner surface side of the first side surface portion.

A method for manufacturing a culture container of one or more embodiments of the the present invention is a method for manufacturing a culture container for a sphere culture. The method includes: performing a first hydrophilic treatment on a part of a film or a sheet made of a polyolefin, and performing a second hydrophilic treatment having a hydrophilic force smaller than a hydrophilic force of the first hydrophilic treatment on another part of the film or the sheet; forming the culture container that has a first side surface portion and a second side surface portion, the first side surface portion having a surface on which the first hydrophilic treatment of the film or the sheet is performed on an inner surface side, the second side surface portion having a surface on which the second hydrophilic treatment is performed on an inner surface side that opposes the first side surface portion, the culture container having a contact angle hysteresis of a surface on the inner surface side of the first side surface portion larger than a contact angle hysteresis of a surface on the inner surface side of the second side surface portion when the contact angle hysteresis is defined as an advance contact angle—a retreat contact angle at a time when water slips; and applying a cell adhesion inhibitor on the inner surface side of the first side surface portion.

In order to achieve the above-described object, a laminated structure of one or more embodiments of the present invention is a laminated structure made by stacking a culture base material having a flexibility. The culture base material is in a film or sheet shape. The culture base material is rolled up into a roll shape to form the laminated structure. The culture base material has a first surface on which a coating layer is formed and a second surface on an opposite side of the first surface. The first surface has a hydrophilicity higher than a hydrophilicity of the second surface.

A method for manufacturing a laminated structure of one or more embodiments of the present invention is a method for manufacturing a laminated structure made by stacking a culture base material having a flexibility. The method includes: performing a hydrophilic treatment on at least a first surface such that a hydrophilicity of the first surface of the culture base material made of a film or a sheet becomes larger than a hydrophilicity of a second surface on an opposite side of the first surface; forming a coating layer by applying a coating agent on the first surface; and rolling up the culture base material in a roll shape.

One or more embodiments of the present invention ensure avoiding a cell adhesion inhibitor applied on one inner surface coming off to be transferred onto another inner surface caused by the inner surfaces of the culture container are brought into contact in manufacturing a culture container made of a flexible packaging material for a sphere culture.

One or more embodiments of the present invention ensure providing a laminated structure that does not cause a transfer of a coating layer formed on a surface of a culture base material in the laminated structure formed by rolling up the culture base material in a roll shape and, a method for manufacturing the same.

BRIEF DESCRIPTION OF THE DRAWINGS

FIG. 1A is an explanatory diagram regarding a static water contact angle.

FIG. 1B is an explanatory diagram regarding a contact angle hysteresis.

FIGS. 2A-2C are drawings illustrating photographs that have taken transferred conditions of a cell adhesion inhibitor in Working Example 1 (FIG. 2A) (Working Example 11) (base material of culture container (culture base material): PE, lower surface (first surface): one corona treatment, upper surface (second surface): no treatment, cell adhesion inhibitor: phospholipid polymer), Working Example 2 (FIG. 2B) (Working Example 12) (base material of culture container: PE, lower surface: three corona treatments, upper surface: no treatment, cell adhesion inhibitor: phospholipid polymer), and Comparative Example 1 (FIG. 2C) (Comparative Example 11) (base material of culture container: PE, lower surface: no treatment, upper surface: no treatment, cell adhesion inhibitor: phospholipid polymer).

FIGS. 3A-3C are drawings illustrating photographs that have taken transferred conditions of a cell adhesion inhibitor in Comparative Example 2 (FIG. 3A) (Comparative Example 12) (base material of culture container (culture base material): PE, lower surface (first surface): no treatment, upper surface (second surface): one corona treatment, cell adhesion inhibitor: phospholipid polymer), Comparative Example 3 (FIG. 3B) (Comparative Example 13) (base material of culture container: PE, lower surface: one corona treatment, upper surface: three corona treatments, cell adhesion inhibitor: phospholipid polymer), and Comparative Example 4 (FIG. 3C) (Comparative Example 14) (base material of culture container: PE, lower surface: three corona treatments, upper surface: three corona treatments, cell adhesion inhibitor: phospholipid polymer).

FIGS. 4A-4B are drawings illustrating photographs that have taken transferred conditions of a cell adhesion inhibitor in Working Example 3 (FIG. 4A) (Working Example 13)

(base material of culture container (culture base material): COC, lower surface (first surface): three corona treatments, upper surface (second surface): no treatment, cell adhesion inhibitor: phospholipid polymer), and Comparative Example 5 (FIG. 4B) (Comparative Example 15) (base material of culture container: COC, lower surface: no treatment, upper surface: no treatment, cell adhesion inhibitor: phospholipid polymer).

FIG. 5A-5B are drawings illustrating photographs that have taken transferred conditions of a cell adhesion inhibitor in Working Example 4 (FIG. 5A) (Working Example 14) (base material of culture container (culture base material): PE, lower surface (first surface): three corona treatments, upper surface (second surface): no treatment, cell adhesion inhibitor: polyvinyl alcohol), and Comparative Example 6 (FIG. 5B) (Comparative Example 16) (base material of culture container: PE, lower surface: no treatment, upper surface: no treatment, cell adhesion inhibitor: polyvinyl alcohol).

FIGS. 6A-6B are drawings illustrating photographs that have taken transferred conditions of a cell adhesion inhibitor in Working Example 5 (FIG. 6A) (Working Example 15) (base material of culture container (culture base material): PE, lower surface (first surface): one corona treatment, upper surface (second surface): no treatment, cell adhesion inhibitor: phospholipid polymer, 50° C., after lapse of seven days), Working Example 6 (FIG. 6B) (Working Example 16) (base material of culture container: PE, lower surface: three corona treatments, upper surface: no treatment, cell adhesion inhibitor: phospholipid polymer, 50° C., after lapse of seven days), and Comparative Example 7 (FIG. 6C) (Comparative Example 17) (base material of culture container: PE, lower surface: no treatment, upper surface: no treatment, cell adhesion inhibitor: phospholipid polymer, 50° C., after lapse of seven days).

FIG. 7 is a drawing illustrating a photograph that has taken a transferred condition of a cell adhesion inhibitor in Working Example 7 (Working Example 17) (base material of culture container (culture base material): PE, lower surface (first surface): one excimer treatment, upper surface (second surface): no treatment, cell adhesion inhibitor: phospholipid polymer).

FIG. 8 is a schematic diagram illustrating a transfer of a cell adhesion inhibitor in a manufacturing step of a conventional culture container.

FIG. 9 is a schematic diagram illustrating a configuration of a laminated structure according to one or more embodiments of the present invention.

FIG. 10 is a schematic diagram illustrating a configuration of another laminated structure according to one or more embodiments of the present invention.

FIG. 11 is a schematic diagram illustrating a method for manufacturing the laminated structure according to one or more embodiments of the present invention (first manufacturing method).

FIG. 12 is a schematic diagram illustrating a method for manufacturing the laminated structure according to one or more embodiments of the present invention (second manufacturing method).

FIG. 13 is a schematic diagram illustrating a state of forming the laminated structure.

FIG. 14 is a schematic diagram illustrating a transfer of a coating layer in the conventional laminated structure.

DETAILED DESCRIPTION OF EMBODIMENTS

The following describes embodiments of a culture container and a method for manufacturing the culture container of the one or more embodiments of the present invention in detail. However, the one or more embodiments of the present invention are not limited to the specific content in the following embodiments.

The culture container of the embodiment is a culture container made of a flexible packaging material. The culture container has a first side surface portion and a second side surface portion that are mutually opposed. At least an inner surface side of the first side surface portion has a surface treatment such that, when a contact angle hysteresis is defined as an advance contact angle—a retreat contact angle at a time when water slips, a contact angle hysteresis of a surface on an inner surface side of the first side surface portion becomes larger than a contact angle hysteresis of a surface on an inner surface side of the second side surface portion, and a membrane made of a cell adhesion inhibitor is formed on the inner surface side of the first side surface portion.

First, a static water contact angle and a contact angle hysteresis will be described with reference to FIG. 1A and FIG. 1B.

The static water contact angle means an angle (θs in FIG. 1A) formed by a liquid surface and a solid surface at a place where a motionless liquid surface contacts a surface of a solid wall. There is a relationship where, when the static water contact angle is large, a hydrophobicity of the surface of the solid wall is relatively strong, and when the static water contact angle is small, a hydrophilicity of the surface of the solid wall is relatively strong.

The contact angle hysteresis means a difference (hysteresis when slipping (θa−θr)) between an advance contact angle (θa) and a retreat contact angle (θr) when water droplet slips on the surface of the solid wall.

That is, it is calculated based on the advance contact angle and the retreat contact angle at a time when a liquid droplet starts to slip when water droplet is dropped on the surface of the solid wall horizontally supported, and the solid wall is gradually inclined. This contact angle hysteresis is used as an index to indicate a dynamic hydrophilicity (wettability) of the surface of the solid wall. There is a relationship where, when the contact angle hysteresis is large, the hydrophilicity of the surface of the solid wall is relatively strong, and when the contact angle hysteresis is small, the hydrophobicity of the surface of the solid wall is relatively strong.

As the flexible packaging material configuring the culture container of one or more embodiments, it may be preferred to use a polyolefin, and more preferred to use a polyethylene (PE), a cyclic olefin copolymer (COC), or the like. In particular, it may be preferred to configure at least an inner surface side of a first side surface portion and an inner surface side of a second side surface portion of the culture container using the polyolefin.

The inner surface side of the first side surface portion and the inner surface side of the second side surface portion configure a surface inside the culture container, and are usually assumed to be used by disposing the culture container with the inner surface side of the first side surface portion serving as a bottom surface when cells are cultured.

That is, since the specific gravity of a culture fluid used in a cell culture is generally smaller than the specific gravity of the cells, when the culture container is left to stand still, the cells precipitate downward. In view of this, the culture container is usually disposed with the inner surface side of the first side surface portion serving as the bottom surface.

On the other hand, if the specific gravity of the culture fluid is larger than the specific gravity of the cells, it is considered that the cells gather on the upper side when the culture container is left to stand still. Therefore, the culture container is disposed with the inner surface side of the first side surface portion serving as an upper surface.

The culture container in the embodiment generally has a bag shape, and has two side surface portions that are mutually opposed. The inner surface side of at least one of the side surface portions has a surface treatment such that contact angle hystereses on the surfaces of the inner surface sides of these side surface portions present different values.

At this time, the surface treatment is performed on the inner surface of the culture container such that the contact angle hysteresis of the surface side (generally, bottom surface side) on which a membrane of the cell adhesion inhibitor is formed becomes larger than the contact angle hysteresis of the opposite surface side (generally, upper surface side) on which the membrane of the cell adhesion inhibitor is not formed in the culture container.

It may be preferred to perform a hydrophilic treatment as a surface treatment. While methods of the hydrophilic treatment include a corona treatment, an excimer treatment, and the like, it is not limited to these.

Specifically, while, for example, the following (A) to (F) are possible, it is not limited to these. Note that, hereinafter, the surface on which the membrane of the cell adhesion inhibitor is formed is referred to as a first side surface, and the surface on which the membrane of the cell adhesion inhibitor is not formed is referred to as a second side surface.

(A) The corona treatment is performed once on the first side surface, and no surface treatment is performed on the second side surface.

(B) The corona treatment is performed three times on the first side surface, and no surface treatment is performed on the second side surface.

(C) The corona treatment is performed three times on the first side surface, and the corona treatment is performed once on the second side surface.

(D) The excimer treatment is performed once on the first side surface, and no surface treatment is performed on the second side surface.

(E) The excimer treatment is performed three times on the first side surface, and no surface treatment is performed on the second side surface.

(F) The excimer treatment is performed three times on the first side surface, and the excimer treatment is performed once on the second side surface.

In the culture container of the embodiment, no surface treatment method as in the following (a) to (k) is performed. The reason is that these surface treatment method cause the contact angle hysteresis of the surface side on which the membrane of the cell adhesion inhibitor is formed to become smaller than or equal to the contact angle hysteresis of the opposite surface side on which the membrane of the cell adhesion inhibitor is not formed.

(a) No surface treatment is performed on the first side surface, and no surface treatment is performed on the second side surface too.

(b) No surface treatment is performed on the first side surface, and the corona treatment is performed once on the second side surface.

(c) No surface treatment is performed on the first side surface, and the corona treatment is performed three times on the second side surface.

(d) The corona treatment is performed once on the first side surface, and the corona treatment is performed once on the second side surface too.

(e) The corona treatment is performed once on the first side surface, and the corona treatment is performed three times on the second side surface.

(f) The corona treatment is performed three times on the first side surface, and the corona treatment is performed three times on the second side surface too.

(g) No surface treatment is performed on the first side surface, and the excimer treatment is performed once on the second side surface.

(h) No surface treatment is performed on the first side surface, and the excimer treatment is performed three times on the second side surface.

(i) The excimer treatment is performed once on the first side surface, and the excimer treatment is performed once on the second side surface too.

(j) The excimer treatment is performed once on the first side surface, and the excimer treatment is performed three times on the second side surface.

(k) The excimer treatment is performed three times on the first side surface, and the excimer treatment is performed three times on the second side surface too.

In the embodiment, as the cell adhesion inhibitor, a phospholipid polymer, a polyvinyl alcohol derivative, a phospholipid-polymer complex, polyhydroxyethylmethacrylate, polyvinyl alcohol, agarose, chitosan, polyethylene glycol, albumin, and the like can be used. They may be combined and used.

It may also be preferred that the culture container of the embodiment has a plurality of wells formed on the inner surface side of the side surface portion on which the membrane of the cell adhesion inhibitor is formed. Forming such wells in the culture container of the embodiment ensures collecting the cells within each of the wells. Therefore, for example, a cell density in an early stage of a sphere culture can be enhanced, thereby ensuring improved sphere forming efficiency.

The method for manufacturing the culture container of the embodiment is a method for manufacturing a culture container for a sphere culture. The method includes: performing a hydrophilic treatment on a part of a film or a sheet made of a polyolefin; forming a culture container that has a first side surface portion having a surface on which the hydrophilic treatment of the film or the sheet is performed on an inner surface side and a second side surface portion that opposes the first side surface portion, and has a contact angle hysteresis of a surface on the inner surface side of the first side surface portion larger than a contact angle hysteresis of a surface on an inner surface side of the second side surface portion when the contact angle hysteresis is defined as an advance contact angle—a retreat contact angle at a time when water slips; and applying a cell adhesion inhibitor on the inner surface side of the first side surface portion.

It may also be preferable that the method for manufacturing the culture container of the embodiment is a method for manufacturing a culture container for a sphere culture. The method includes: performing a first hydrophilic treatment on a part of a film or a sheet made of a polyolefin, and performing a second hydrophilic treatment having a hydrophilic force smaller than a hydrophilic force of the first hydrophilic treatment on another part of the film or the sheet; forming a culture container that has a first side surface portion having a surface on which the first hydrophilic treatment of the film or the sheet is performed on an inner surface side and a second side surface portion opposing the first side surface portion and having a surface on which the second hydrophilic treatment is performed on an inner surface side, and has a contact angle hysteresis of a surface on the inner surface side of the first side surface portion larger than a contact angle hysteresis of a surface on the inner surface side of the second side surface portion when the contact angle hysteresis is defined as an advance contact angle—a retreat contact angle at a time when water slips; and applying a cell adhesion inhibitor on the inner surface side of the first side surface portion.

That is, in the method for manufacturing the culture container of the embodiment, the hydrophilic treatment is performed on a part of the film or the sheet made of the polyolefin, and the culture container is made into a bag using this film or sheet, to form the culture container having the side surface portions with the different contact angle hysteresis values.

Specifically, the culture container that has the contact angle hysteresis of the surface side (inner surface side of first side surface portion, generally, bottom surface side) on which the membrane of the cell adhesion inhibitor is formed larger than the contact angle hysteresis of the opposite surface side (inner surface side of second side surface portion, generally, upper surface side) on which the membrane of the cell adhesion inhibitor is not formed is formed.

Applying the cell adhesion inhibitor on such an inner surface side of the first side surface portion of the culture container ensures manufacturing the culture container in which the membrane of the cell adhesion inhibitor does not easily come off.

Accordingly, the method for manufacturing the culture container of the embodiment ensures manufacturing the culture container in which the sphere can be formed.

As described above, the culture container and the method for manufacturing the culture container of the embodiment ensure obtaining the culture container that has the contact angle hysteresis of the surface on which the membrane of the cell adhesion inhibitor is formed larger than the contact angle hysteresis of the opposite surface on which the membrane of the cell adhesion inhibitor is not formed in the culture container.

The cell adhesion inhibitor applied on such a culture container does not come off of the application surface to be transferred onto the opposite surface side, thereby ensuring an appropriate sphere culture.

Next, embodiments of a laminated structure and a method for manufacturing the laminated structure of the one or more embodiments of present invention will be described in detail. However, one or more embodiments of the present invention are not limited to the specific content of the following embodiment.

The laminated structure of the embodiment is a laminated structure made by stacking a culture base material having a flexibility. The culture base material is in a film or sheet shape. The culture base material is rolled up into a roll shape to form the laminated structure. The culture base material has a first surface on which a coating layer is formed and a second surface on an opposite side of the first surface. The first surface has a hydrophilicity higher than a hydrophilicity of the second surface.

That is, when the contact angle hysteresis is defined as the advance contact angle—the retreat contact angle, the hysteresis of the first surface is larger than the hysteresis of the second surface.

The second surface and the coating layer are in a state of closely in contact without adhering.

The laminated structure of the embodiment may be made of a multilayer film, and can be used as a packaging material to form the culture container and the like.

The laminated structure in the embodiment is formed by laminating a culture base material 1 on which a coating layer 2 is formed on a surface as illustrated in FIG. 9. Note that FIG. 9 illustrates only a part of the laminated structure of the embodiment. While the laminated structure in the same drawing has four layers of the culture base materials 1, it is not limited to this, and the laminated structure may have two layers, three layers, or five layers or more.

Such a laminated structure can be formed by rolling up the culture base material 1 on which the coating layer 2 is formed on the surface into a roll shape. In the same drawing, the coating layer 2 other than the uppermost layer is adhered on a surface 11 of the culture base material 1 under the coating layer 2, however, is closely in contact with a lower surface of the culture base material 1 above the coating layer 2 without adhering.

A surface 11 (first surface) of the culture base material 1 has the hydrophilic treatment. This relatively decreases the static water contact angle compared with a case without performing the hydrophilic treatment, and thus, a state where the contact angle hysteresis is relatively increased is provided. While the hydrophilic treatment can be performed with, for example, the corona treatment or the excimer treatment, it is not limited to these.

The coating layer 2 is formed by applying a coating agent on the surface 11 of the culture base material 1 on which the hydrophilic treatment is thus performed.

The laminated structure of the embodiment has the contact angle hysteresis of the surface 11 of the culture base material 1 is in a state relatively larger than a contact angle hysteresis of the surface 12 (surface on opposite side of surface on which the coating layer 2 is formed in the culture base material 1) (second surface) of the culture base material 1 by performing the hydrophilic treatment on the surface 11 of the culture base material 1 as described above.

Thus, the laminated structure of the embodiment has the contact angle hysteresis of the surface 11 of the culture base material 1 larger than the contact angle hysteresis of the surface 12 of the culture base material 1. Therefore, when the culture base material 1 is spread into a planar shape when in use, a transfer of the coating layer 2 formed onto the surface 11 of the culture base material 1 on the surface 12 of the culture base material 1 can be avoided.

Accordingly, the laminated structure of the embodiment ensures avoiding the coating layer 2 formed on the surface 11 of the culture base material 1 adhering onto the surface 12 of the culture base material 1 to come off of the surface 11.

As a material that configure the culture base material 1, it may be preferred to use the polyolefin, and it is more preferred to use the polyethylene (PE), the cyclic olefin copolymer (COC), and the like. In particular, it may be preferred to configure at least a side of the surface 11 of the culture base material 1 using the polyolefin.

As a coating agent that forms the coating layer 2, it is not specifically limited, and, for example, the cell adhesion inhibitor can be employed. As this cell adhesion inhibitor, the phospholipid polymer, the polyvinyl alcohol derivative, the phospholipid-polymer complex, the polyhydroxyethyl-methacrylate, the polyvinyl alcohol, the agarose, the chitosan, the polyethylene glycol, the albumin, and the like can be used. They may be combined and used.

The culture base material can be made of a plurality of identical or different base material layers. Specifically, as illustrated in FIG. 10, the culture base material can be formed by adhering the culture base material 1 and a culture base material 1a. It is possible to form the culture base material by adhering more culture base materials. At this time, the contact angle hysteresis of the surface 11 of the culture base material 1 is larger than a contact angle hysteresis of a surface 12*a* (or bottom surface of culture base material on the lowermost side) (second surface) of the culture base material 1*a*.

As a material that configure the culture base material 1*a* and another culture base material, it may also be preferred to use the polyolefin, and it may be more preferred to use the polyethylene (PE), the cyclic olefin copolymer (COC), and the like.

Even when the culture base material is thus made of the plurality of base material layers, it is possible to avoid the coating layer 2 adhering onto the second surface of the culture base material to come off.

The method for manufacturing the laminated structure of the embodiment is a method for manufacturing a laminated structure made by stacking culture base materials having a flexibility. The method includes: performing a hydrophilic treatment on at least a first surface such that a hydrophilicity of the first surface of the culture base material made of a film or a sheet becomes larger than a hydrophilicity of a second surface on an opposite side of the first surface; forming a coating layer by applying a coating agent on the first surface; and rolling up the culture base material into a roll shape.

Specifically, as illustrated in FIG. 11, the hydrophilic treatment is performed on the surface 11 of the culture base material 1 to cause the contact angle hysteresis of the surface 11 of the culture base material 1 to be in a state larger than the contact angle hysteresis of the surface 12 of the culture base material 1. In the example in the same drawing, the hydrophilic treatment is not performed on the surface 12 of the culture base material 1. Next, the coating layer 2 is formed on the surface 11 of the culture base material 1. Note that the culture base material may be made of the plurality of base material layers. The same applies to the following.

Rolling up the culture base material 1 thus obtained into a roll shape ensures obtaining the laminated structure of the embodiment.

As illustrated in FIG. 12, it is possible to perform the hydrophilic treatment on the surface 12 of the culture base material 1. In this case, a hydrophilic treatment B with a hydrophilic force smaller than that of a hydrophilic treatment A on the surface 11 of the culture base material 1 is performed on the surface 12 of the culture base material 1. That is, the hydrophilic treatment is performed on the surface 12 of the culture base material 1 such that the hydrophilicity of the surface 12 of the culture base material 1 becomes smaller than the hydrophilicity of the surface 11 of the culture base material 1.

As the result, the laminated structure having the hydrophilicity of the surface 11 of the culture base material 1 in a state larger than the hydrophilicity of the surface 12 of the culture base material 1 can be obtained.

This makes a close contactness of the surface 11 of the culture base material 1 with the coating layer 2 stronger than that of the surface 12 of the culture base material 1, thereby ensuring avoiding the coating layer 2 adhering onto the surface 12 to come off of the surface 11.

That is, with any cases of the methods illustrated in FIG. 11 and FIG. 12, the hydrophilic treatment is performed on the surface 11 of the culture base material 1 such that the contact angle hysteresis of the surface 11 of the culture base material 1 becomes larger than the contact angle hysteresis of the surface 12 of the culture base material 1 in the method for manufacturing the laminated structure of the embodiment. Specifically, while, for example, the following (I) to (VI) are possible, it is not limited to these.

(I) The corona treatment is performed once on the surface 11, and no hydrophilic treatment is performed on the surface 12.

(II) The corona treatment is performed three times on the surface 11, and no hydrophilic treatment is performed on the surface 12.

(III) The corona treatment is performed three times on the surface 11, and the corona treatment is performed once on the surface 12.

(IV) The excimer treatment is performed once on the surface 11, and no hydrophilic treatment is performed on the surface 12.

(V) The excimer treatment is performed three times on the surface 11, and no hydrophilic treatment is performed on the surface 12.

(VI) The excimer treatment is performed three times on the surface 11, and the excimer treatment is performed once on the surface 12.

In the method for manufacturing the laminated structure of the embodiment, no hydrophilic treatment as in the following (i) to (ix) is performed. The reason is that the contact angle hysteresis of the surface 11 becomes smaller than or equal to the contact angle hysteresis of the surface 12.

(i) No hydrophilic treatment is performed on the surface 11, and no hydrophilic treatment is performed on the surface 12 too.

(ii) No hydrophilic treatment is performed on the surface 11, and the corona treatment is performed once on the surface 12.

(iii) The corona treatment is performed once on the surface 11, and the corona treatment is performed once on the surface 12 too.

(iv) The corona treatment is performed once on the surface 11, and the corona treatment is performed three times on the surface 12.

(v) The corona treatment is performed three times on the surface 11, and the corona treatment is performed three times on the surface 12 too.

(vi) No hydrophilic treatment is performed on the surface 11, and the excimer treatment is performed once on the surface 12.

(vii) The excimer treatment is performed once on the surface 11, and the excimer treatment is performed once on the surface 12 too.

(viii) The excimer treatment is performed once on the surface 11, and the excimer treatment is performed three times on the surface 12.

(ix) The excimer treatment is performed three times on the surface 11, and the excimer treatment is performed three times on the surface 12 too.

Here, in the embodiment, the hydrophilicity is determined by the contact angle hysteresis. The reason is that, it is considered that, the static water contact angle has a correlation with an amount of hydrophilic functional group in the outermost layer while in contact with the air, and therefore, if the functional group dives into the resin over time, the value changes even in a hydrophobic side.

On the other hand, it is considered that, the contact angle hysteresis has a correlation with an amount of hydrophilic functional group in the outermost layer and a slightly inside, and therefore, even if the functional group dives into the resin over time, the value hardly changes.

In the method for manufacturing the laminated structure of the embodiment, as a method for forming the culture base material made of the plurality of layers, a multi-layer extrusion or a lamination method can be used.

In the multi-layer extrusion, for example, a plurality of kinds of resins are injected into respective independent extruders, and the plurality of kinds of resins are extruded into a multi-layer T-Die from these extruders. The multi-layer T-Die flows the melted resin, and rolling this up ensures obtaining the culture base material formed of the plurality of layers.

In the lamination method, press-bonding the films separately formed while heating them ensures obtaining the culture base material formed of the plurality of layers. Note that, in this case, while an adhesive is used in the case where completely different kinds of resins, such as PE and nylon, and PE and PET, are laminated, the adhesive is not necessary for, for example, PE and hydrophilic treatment PE since they are resins having the same property.

As described above, with the laminated structure and the method for manufacturing the laminated structure of the embodiment, it is possible to avoid the coating layer formed on the surface of the culture base material coming off to be transferred in the laminated structure formed by rolling up the culture base material into a roll shape.

Furthermore, the films are sent out from the above-described laminated structure to be heat-sealed on three corners or four corners, and thus, two films are attached together to ensure providing a bag shaped container configuration.

The coating layer may coat the whole surface of the surface 11 or may selectively coat only a non-heat-seal region. The laminated structure is appropriately used as a packaging material.

WORKING EXAMPLES

A detailed description will be given of experiments that were performed to confirm that the cell adhesion inhibitor does not come off of the surface on which the cell adhesion inhibitor is applied to be transferred onto the opposite surface when the contact angle hysteresis of the surface on which the membrane of the cell adhesion inhibitor is formed is larger than the contact angle hysteresis of the opposite surface on which the membrane of the cell adhesion inhibitor is not formed in the culture container according to the one or more embodiments of the present invention.

Working Example 1

A rectangular film made of the polyolefin was prepared, and, as illustrated in FIG. 2, the left half side square portion was assumed to be a bottom surface in the culture container and the right half side square portion was assumed to be an upper surface in the culture container. After the cell adhesion inhibitor was applied on the bottom surface, the upper surface was placed over the bottom surface, and a load was applied on them. Afterwards, the upper surface was peeled off of the bottom surface to determine whether the cell adhesion inhibitor was transferred onto the upper surface or not by a visual observation. Specifically, it was performed as follows.

First, a polyethylene (PE) film was used as the film. As the surface treatment, the corona treatment was performed once on the bottom surface using a batch-type corona treater (manufactured by KASUGA DENKI, Inc., the same applies to the following). No surface treatment was performed on the upper surface.

At this time, the static water contact angle of the bottom surface was 71.9 degrees, and the contact angle hysteresis was 43.6 degrees. The static water contact angle of the upper surface was 96.7 degrees, and the contact angle hysteresis was 18.0 degrees.

A solid-liquid interface analysis system DropMaster 700 (manufactured by Kyowa Interface Science Co., Ltd) was used for measuring the static water contact angle and hysteresis.

Specifically, the static water contact angle ($\theta s$) was measured by dropping 3 μl of pure water on the film. The contact angle hysteresis ($\theta a - \theta r$) was obtained by dropping 30 μl of pure water on the film, inclining a measurement stand one degree for each second, and calculating the advance contact angle ($\theta a$) and the retreat contact angle ($\theta r$) at the time of slipping by a tangential method.

Next, after forming a membrane by applying a phospholipid polymer (LIPIDURE (registered trademark), NOF CORPORATION) ethanol solution prepared to be 0.5% as the cell adhesion inhibitor on the bottom surface with a bar coater, this membrane of the cell adhesion inhibitor was dyed with a coomassie blue and dried.

After the upper surface was attached to this bottom surface, and a load of 10 g/cm$^2$ was applied to be left to stand still for one minute, the upper surface was peeled off of the bottom surface.

As the result, the membrane of the cell adhesion inhibitor formed on the bottom surface was not transferred onto the upper surface. It is considered that, in this experiment, hydrophilizing the bottom surface improved the close contactness between the base material of the bottom surface and the cell adhesion inhibitor, while the upper surface remained hydrophobic, and therefore, the cell adhesion inhibitor was not transferred from the bottom surface onto the upper surface, and was not peeled off.

Working Example 2

The condition of the surface treatment was made different from that of Working Example 1, the other conditions were made similar to those of Working Example 1, and the experiment was performed.

Specifically, the polyethylene (PE) film was used as the film. As the surface treatment, the corona treatment was performed three times on the bottom surface using the batch-type corona treater. No surface treatment was performed on the upper surface.

At this time, the static water contact angle of the bottom surface was 54.2 degrees, and the contact angle hysteresis was 50.3 degrees. The static water contact angle of the upper surface was 96.7 degrees, and the contact angle hysteresis was 18.0 degrees.

As the result, the membrane of the cell adhesion inhibitor formed on the bottom surface was not transferred. It is considered that, in this experiment, more strongly hydrophilizing the bottom surface further improved the close contactness between the base material of the bottom surface and the cell adhesion inhibitor, while the upper surface remained hydrophobic, and therefore, the cell adhesion inhibitor was not transferred from the bottom surface onto the upper surface, and was not peeled off.

Comparative Example 1

The condition of the surface treatment was made different from that of Working Example 1, the other conditions were made similar to those of Working Example 1, and the experiment was performed.

Specifically, the polyethylene (PE) film was used as the film. No surface treatment was performed on the bottom surface and the upper surface.

At this time, the static water contact angles on the bottom surface and the upper surface were 96.7 degrees, and the contact angle hystereses were 18.0 degrees.

As the result, the membrane of the cell adhesion inhibitor formed on the bottom surface was largely transferred onto the upper surface. It is considered that, in this experiment, both the bottom surface and the upper surface remained hydrophobic, and therefore, the base material of the bottom surface and the cell adhesion inhibitor did not sufficiently adhere, and the cell adhesion inhibitor was transferred onto the upper surface to be peeled off of the bottom surface.

Comparative Example 2

The condition of the surface treatment was made different from that of Working Example 1, the other conditions were made similar to those of Working Example 1, and the experiment was performed.

Specifically, the polyethylene (PE) film was used as the film. No surface treatment was performed on the bottom surface. On the other hand, as the surface treatment, the corona treatment was performed three times on the upper surface using the batch-type corona treater.

At this time, the static water contact angle of the bottom surface was 96.7 degrees, and the contact angle hysteresis was 18.0 degrees. The static water contact angle of the upper surface was 54.2 degrees, and the contact angle hysteresis was 50.3 degrees.

As the result, the membrane of the cell adhesion inhibitor formed on the bottom surface was largely transferred on the upper surface. It is considered that, in this experiment, while the bottom surface remained hydrophobic, the upper surface was strongly hydrophilized, and therefore, the membrane of the cell adhesion inhibitor formed on the bottom surface was transferred onto the upper surface, and was peeled off of the bottom surface.

Comparative Example 3

The condition of the surface treatment was made different from that of Working Example 1, the other conditions were made similar to those of Working Example 1, and the experiment was performed.

Specifically, the polyethylene (PE) film was used as the film. As the surface treatment, the corona treatment was performed once on the bottom surface using the batch-type corona treater, and as the surface treatment, the corona treatment was performed three times on the upper surface using the batch-type corona treater.

At this time, the static water contact angle of the bottom surface was 71.9 degrees, and the contact angle hysteresis was 43.6 degrees. The static water contact angle of the upper surface was 54.2 degrees, and the contact angle hysteresis was 50.3 degrees.

As the result, the membrane of the cell adhesion inhibitor formed on the bottom surface was largely transferred onto the upper surface. It is considered that, in this experiment, the upper surface was more strongly hydrophilized than the bottom surface, and therefore, the membrane of the cell adhesion inhibitor formed on the bottom surface was transferred onto the upper surface, and was peeled off of the bottom surface.

Comparative Example 4

The condition of the surface treatment was made different from that of Working Example 1, the other conditions were made similar to those of Working Example 1, and the experiment was performed.

Specifically, the polyethylene (PE) film was used as the film. As the surface treatment, the corona treatment was performed three times on the bottom surface and the upper surface using the batch-type corona treater.

At this time, the static water contact angles of the bottom surface and the upper surface were 54.2 degrees, and the contact angle hystereses were 50.3 degrees.

As the result, the membrane of the cell adhesion inhibitor formed on the bottom surface was largely transferred onto the upper surface. It is considered that, in this experiment, both the bottom surface and the upper surface were similarly and strongly hydrophilized, and therefore, the membrane of the cell adhesion inhibitor formed on the bottom surface was transferred onto the upper surface, and was peeled off of the bottom surface.

Thus, from the results of Comparative Examples 2 to 4, it was found that the cell adhesion inhibitor was easily peeled off of the bottom surface when the upper surface was strongly hydrophilized.

Working Example 3

The conditions of the film material and the surface treatment was made different from those of Working Example 1, the other conditions were made similar to those of Working Example 1, and the experiment was performed.

Specifically, the cyclic olefin copolymer (COC) film was used as the film. As the surface treatment, the corona treatment was performed three times on the bottom surface using the batch-type corona treater. No surface treatment was performed on the upper surface.

At this time, the static water contact angle of the bottom surface was 55.2 degrees, and the contact angle hysteresis was 48.8 degrees. The static water contact angle of the upper surface was 97.0 degrees, and the contact angle hystereses was 22.6 degrees.

As the result, the membrane of the cell adhesion inhibitor formed on the bottom surface was not transferred onto the upper surface. It is considered that, in this experiment, hydrophilizing the bottom surface improved the close contactness between the base material of the bottom surface and the cell adhesion inhibitor, while the upper surface remained hydrophobic, and therefore, the cell adhesion inhibitor was not transferred from the bottom surface onto the upper surface, and was not peeled off.

Comparative Example 5

The condition of the surface treatment was made different from that of Working Example 3, the other conditions were made similar to those of Working Example 3, and the experiment was performed.

Specifically, the cyclic olefin copolymer (COC) film was used as the film. No surface treatment was performed on the bottom surface and the upper surface.

At this time, the static water contact angles of the bottom surface and the upper surface were 97.0 degrees, and the contact angle hystereses were 22.6 degrees.

As a result, the membrane of the cell adhesion inhibitor formed on the bottom surface was slightly transferred onto the upper surface. It is considered that, in this experiment, both the bottom surface and the upper surface remained hydrophobic, and therefore, the base material of the bottom surface and the cell adhesion inhibitor did not sufficiently adhere, and the cell adhesion inhibitor was transferred onto the upper surface to be peeled off of the bottom surface.

Working Example 4

The conditions of the kind of the cell adhesion inhibitor, its coating method, and the surface treatment were made different from those of Working Example 1, the other conditions were made similar to those of Working Example 1, and the experiment was performed.

Specifically, the polyethylene (PE) film was used as the film. As the surface treatment, the corona treatment was performed three times on the bottom surface using the batch-type corona treater. No surface treatment was performed on the upper surface.

At this time, the static water contact angle of the bottom surface was 54.2 degrees, and the contact angle hysteresis was 50.3 degrees. The static water contact angle of the upper surface was 96.7 degrees, and the contact angle hysteresis was 18.0 degrees.

As the cell adhesion inhibitor, polyvinyl alcohol (BIO-SURFINE (registered trademark)—AWP, Toyo Gosei Co., Ltd) that has an azido group in a side chain was used. After preparing this cell adhesion inhibitor into water solution of 1% and applying the cell adhesion inhibitor onto the bottom surface with the bar coater, the bottom surface was irradiated with a UV having a wavelength of 254 nm at a light amount of 0.7 J/cm$^2$ to be cured.

As the result, the membrane of the cell adhesion inhibitor formed on the bottom surface was not transferred onto the upper surface. It is considered that, in this experiment, hydrophilizing the bottom surface improved the close contactness between the base material of the bottom surface and the cell adhesion inhibitor, while the upper surface remained hydrophobic, and therefore, the cell adhesion inhibitor was not transferred from the bottom surface onto the upper surface, and was not peeled off.

That is, even in the case where the kind of the cell adhesion inhibitor was made different, performing the hydrophilic treatment on the bottom surface ensured avoiding the transfer of the cell adhesion inhibitor from the bottom surface onto the upper surface.

Comparative Example 6

The condition of the surface treatment was made different from that of Working Example 4, and the other conditions were made similar to those of Working Example 4, and the experiment was performed.

Specifically, the polyethylene (PE) film was used as the film. No surface treatment was performed on the bottom surface and the upper surface.

At this time, the static water contact angles of the bottom surface and the upper surface were 96.7 degrees, and contact angle hystereses were 18.0 degrees.

As the cell adhesion inhibitor, polyvinyl alcohol (BIO-SURFINE (registered trademark)—AWP, Toyo Gosei Co., Ltd) that has an azido group in a side chain was used. After preparing this cell adhesion inhibitor into water solution of 1% and applying the cell adhesion inhibitor onto the bottom surface with the bar coater, the bottom surface was irradiated with a UV having a wavelength of 254 nm at a light amount of 0.7 J/cm$^2$ to be cured.

As the result, the membrane of the cell adhesion inhibitor formed on the bottom surface was slightly transferred onto the upper surface. It is considered that, in this experiment, both the bottom surface and the upper surface remained hydrophobic, and therefore, the base material of the bottom surface and the cell adhesion inhibitor did not sufficiently adhere, and the cell adhesion inhibitor was transferred onto the upper surface to be peeled off of the bottom surface.

Working Example 5

After performing the surface treatment on a film with the same condition as that of Working Example 1, the static water contact angles and the contact angle hystereses of the bottom surface and the upper surface were measured after a lapse of seven days at 50° C.

Specifically, the polyethylene (PE) film was used as the film. As the surface treatment, the corona treatment was performed once on the bottom surface using the batch-type corona treater. No surface treatment was performed on the upper surface.

After a lapse of seven days at 50° C., the static water contact angle of the bottom surface on which the corona treatment was performed once was 87.8 degrees, and the contact angle hysteresis was 43.9 degrees. The static water contact angle of the upper surface on which no surface treatment was performed was 96.7 degrees, and the contact angle hysteresis was 18.0 degrees.

That is, as the result of storing the film on which the surface treatment was performed on the bottom surface for seven days at 50° C., it can be found that the static water contact angle of the bottom surface is recovered to a value indicating the hydrophobicity, which is close to a value without the surface treatment. In contrast to this, no large change was seen in the contact angle hysteresis of the bottom surface compared with Working Example 1.

Next, similar to Working Example 1, after applying the cell adhesion inhibitor to form a membrane on the bottom surface, this membrane of the cell adhesion inhibitor was dyed with a coomassie blue and dried.

After the upper surface was attached to this bottom surface, and a load of 10 g/cm$^2$ was applied to be left to stand still for one minute, the upper surface was peeled off of the bottom surface.

As the result, the membrane of the cell adhesion inhibitor formed on the bottom surface was not transferred onto the upper surface.

That is, it is considered that, while the static water contact angle of the bottom surface was recovered to the value indicating the hydrophobicity, the contact angle hysteresis of the bottom surface presented a hydrophilized value, and thus, the close contactness between the base material of the bottom surface and the cell adhesion inhibitor improved, while the upper surface remained hydrophobic, and therefore, the cell adhesion inhibitor was not transferred from the bottom surface onto the upper surface, and was not peeled off.

Here, it is considered that, the static water contact angle has a correlation with an amount of hydrophilic functional group in the outermost layer while in contact with the air, and therefore, as the result of the functional group diving into the resin over time, the value changed even to the value indicating the hydrophobicity.

On the other hand, it is considered that, the contact angle hysteresis has a correlation with an amount of hydrophilic functional group in the outermost layer and a slightly inside, and therefore, even if the functional group dived into the resin over time, the value hardly changed.

It has become apparent that, when while the static water contact angle of the bottom surface thus presents the value of hydrophobicity, the contact angle hysteresis of the bottom surface presents the hydrophilized value, it can be said that the bottom surface is hydrophilized, as described above.

Working Example 6

The condition of the surface treatment was made different from that of Working Example 5, and the other conditions were made similar to those of Working Example 5, and the experiment was performed.

Specifically, the polyethylene (PE) film was used as the film. As the surface treatment, the corona treatment was performed three times on the bottom surface using the batch-type corona treater. No surface treatment was performed on the upper surface. After a lapse of seven days at 50° C., the static water contact angles and the contact angle hystereses of the bottom surface and the upper surface were measured.

At this time, the static water contact angle of the bottom surface on which the corona treatment was performed three times was 85.3 degrees, and the contact angle hysteresis was 44.5 degrees. The static water contact angle of the upper surface on which no surface treatment was performed was 96.7 degrees, and the contact angle hysteresis was 18.0 degrees.

That is, as the result of storing the film on which the surface treatment was performed on the bottom surface for seven days at 50° C., it can be seen that the static water contact angle of the bottom surface is recovered to a value indicating the hydrophobicity, which is close to a value without the surface treatment. In contrast to this, no large change was seen in the contact angle hysteresis of the bottom surface.

Next, similar to Working Example 1, after applying the cell adhesion inhibitor to form a membrane on the bottom surface, this membrane of the cell adhesion inhibitor was dyed with a coomassie blue and dried.

After the upper surface was attached to this bottom surface, and a load of 10 g/cm² was applied to be left to stand still for one minute, the upper surface was peeled off of the bottom surface.

As the result, the membrane of the cell adhesion inhibitor formed on the bottom surface was not transferred onto the upper surface similarly to Working Example 5.

That is, it is considered that, while the static water contact angle of the bottom surface was recovered to the value indicating the hydrophobicity, the contact angle hysteresis of the bottom surface presented a hydrophilized value, and thus, the close contactness between the base material of the bottom surface and the cell adhesion inhibitor improved, while the upper surface remained hydrophobic, and therefore, the cell adhesion inhibitor was not transferred from the bottom surface onto the upper surface, and was not peeled off.

Comparative Example 7

The condition of the surface treatment was made different from that of Working Example 5, the other conditions were made similar to those of Working Example 5, and the experiment was performed.

Specifically, the polyethylene (PE) film was used as the film. No surface treatment was performed on the bottom surface and the upper surface. After a lapse of seven days at 50° C., the static water contact angles and the contact angle hystereses of the bottom surface and the upper surface were measured.

At this time, the static water contact angles of the bottom surface and the upper surface were 96.7 degrees, and the contact angle hystereses were 18.0 degrees.

Next, similar to Working Example 1, after applying the cell adhesion inhibitor to form the membrane on the bottom surface, this membrane of the cell adhesion inhibitor was dyed with a coomassie blue and dried.

After the upper surface was attached to this bottom surface, and a load of 10 g/cm² was applied to be left to stand still for one minute, the upper surface was peeled off of the bottom surface.

As the result, the membrane of the cell adhesion inhibitor formed on the bottom surface was transferred onto the upper surface. It is considered that, in this experiment, both the bottom surface and the upper surface remained hydrophobic, and therefore, the base material of the bottom surface and the cell adhesion inhibitor did not sufficiently adhere, and the cell adhesion inhibitor was transferred onto the upper surface to be peeled off of the bottom surface.

Working Example 7

The condition of the surface treatment was made different from that of Working Example 1, the other conditions were made similar to those of Working Example 1, and the experiment was performed.

Specifically, the polyethylene (PE) film was used as the film. As the surface treatment, the excimer treatment was performed once on the bottom surface using an excimer irradiation apparatus (made by the M. D. COM. Inc.). At this time, the conditions of the excimer treatment were 12 V, an irradiation distance of 4 mm, and a table moving speed of 5 mm/sec. No surface treatment was performed on the upper surface.

At this time, the static water contact angle of the bottom surface was 76.2 degrees, and the contact angle hysteresis was 41.8 degrees. The static water contact angle of the upper surface was 96.7 degrees, and the contact angle hysteresis was 18.0 degrees.

As the result, the membrane of the cell adhesion inhibitor formed on the bottom surface was not transferred onto the upper surface. It is considered that, in this experiment, hydrophilizing the bottom surface improved the close contactness between the base material of the bottom surface and the cell adhesion inhibitor, while the upper surface remained hydrophobic, and therefore, the cell adhesion inhibitor was not transferred from the bottom surface onto the upper surface, and was not peeled off.

That is, even in the case where the hydrophilic treatment method was made different from the corona treatment, performing the hydrophilic treatment on the bottom surface ensured avoiding the transfer of the cell adhesion inhibitor from the bottom surface onto the upper surface.

As described above, it has become apparent that hydrophilizing only the bottom surface or more strongly hydrophilizing the bottom surface than the upper surface inside the culture container ensures relatively improving the close contactness between the base material of the bottom surface and the cell adhesion inhibitor more than the close contactness between the base material of the upper surface and the cell adhesion inhibitor, and thus, the cell adhesion inhibitor was not transferred from the bottom surface onto the upper surface, and the peeling was able to be avoided. On the other hand, it has become apparent that strongly hydrophilizing the upper surface inside the culture container caused the cell adhesion inhibitor to be easily peeled off of the bottom surface.

It was found that, even in the case where the kind of the cell adhesion inhibitor was made different, hydrophilizing only the bottom surface or more strongly hydrophilizing the bottom surface than the upper surface inside the culture container ensures avoiding the transfer of the cell adhesion inhibitor from the bottom surface onto the upper surface.

Next, a detailed description will be given of experiments performed to confirm that the coating layer does not come off of the surface on which the coating layer is formed to be transferred on the surface on the opposite side as long as the contact angle hysteresis of the surface on which the coating layer is formed of the culture base material 1 is larger than the contact angle hysteresis of the surface on which the coating layer is not formed on the opposite side of the surface, in the laminated structure according to the one or more embodiments of the present invention.

Note that, while Working Examples 11 to 17 and Comparative Examples 11 to 17 described below are the same experiment as the above-described Working Examples 1 to 7 and Comparative Examples 1 to 7, respectively, the terms used in the respective corresponding embodiments are different, and therefore, descriptions will be given again.

Working Example 11

A rectangular film made of the polyolefin was prepared, and, as illustrated in FIG. 2, the left half side square portion was assumed to be the surface 11 of the culture base material 1 and the right half side square portion was assumed to be the surface 12 of the culture base material 1. After the cell adhesion inhibitor was applied on the surface 11, the surface 12 was placed over the surface 11, and a load was applied on them. Afterwards, the surface 12 was peeled off of the surface 11 to determine whether the cell adhesion inhibitor was transferred onto the surface 12 or not by a visual observation. Specifically, it was performed as follows.

First, the polyethylene (PE) film was used as the film. As the surface treatment, the corona treatment was performed once on the surface 11 using the batch-type corona treater (made by KASUGA DENKI, Inc., the same applies to the following). No surface treatment was performed on the surface 12.

At this time, the static water contact angle of the surface 11 was 71.9 degrees, and the contact angle hysteresis was 43.6 degrees. The static water contact angle of the surface 12 was 96.7 degrees, and the contact angle hysteresis was 18.0 degrees.

The solid-liquid interface analysis system DropMaster 700 (manufactured by Kyowa Interface Science Co., Ltd) was used for measuring the static water contact angle and hysteresis.

Specifically, the static water contact angle (θs) was measured by dropping 3 μl of pure water on the film. The contact angle hysteresis (θa−θr) was obtained by dropping 30 μl of pure water on the film, inclining a measurement stand one degree for each second, and calculating the advance contact angle (θa) and the retreat contact angle (θr) at the time of slipping by the tangential method.

Next, after forming a membrane by applying a phospholipid polymer (LIPIDURE (registered trademark), NOF CORPORATION) ethanol solution prepared to be 0.5% as the cell adhesion inhibitor on the surface 11 with the bar coater, this membrane of the cell adhesion inhibitor was dyed with a coomassie blue and dried.

After the surface 12 was attached to this surface 11, and a load of 10 g/cm$^2$ was applied to be left to stand still for one minute, the surface 12 was peeled off of the surface 11.

As the result, the membrane of the cell adhesion inhibitor (coating layer) formed on the surface 11 was not transferred onto the surface 12. It is considered that, in this experiment, hydrophilizing the surface 11 improved the close contactness between the base material of the surface 11 and the cell adhesion inhibitor, while the surface 12 remained hydrophobic, and therefore, the cell adhesion inhibitor was not transferred from the surface 11 onto the surface 12, and was not peeled off.

Working Example 12

The condition of the surface treatment was made different from that of Working Example 11, the other conditions were made similar to those of Working Example 11, and the experiment was performed.

Specifically, the polyethylene (PE) film was used as the film. As the surface treatment, the corona treatment was performed three times on the surface 11 using the batch-type corona treater. No surface treatment was performed on the surface 12.

At this time, the static water contact angle of the surface 11 was 54.2 degrees, and the contact angle hysteresis was 50.3 degrees. The static water contact angle of the surface 12 was 96.7 degrees, and the contact angle hysteresis was 18.0 degrees.

As the result, the membrane of the cell adhesion inhibitor formed on the surface 11 was not transferred onto the back side. It is considered that, in this experiment, more strongly hydrophilizing the surface 11 further improved the close contactness between the base material of the surface 11 and the cell adhesion inhibitor, while the surface 12 remained hydrophobic, and therefore, the cell adhesion inhibitor was not transferred from the surface 11 onto the surface 12, and was not peeled off.

Comparative Example 11

The condition of the surface treatment was made different from that of Working Example 11, the other conditions were made similar to those of Working Example 11, and the experiment was performed.

Specifically, the polyethylene (PE) film was used as the film. No surface treatment was performed on the surface 11 and the surface 12.

At this time, the static water contact angles of the surface 11 and the surface 12 were 96.7 degrees, and the contact angle hystereses were 18.0 degrees.

As the result, the membrane of the cell adhesion inhibitor formed on the surface 11 was largely transferred onto the surface 12. It is considered that, in this experiment, both the surface 11 and the surface 12 remained hydrophobic, and therefore, the base material of the surface 11 and the cell adhesion inhibitor did not sufficiently adhere, and the cell adhesion inhibitor was transferred onto the surface 12 to be peeled off of the surface 11.

Comparative Example 12

The condition of the surface treatment was made different from that of Working Example 11, the other conditions were made similar to those of Working Example 11, and the experiment was performed.

Specifically, the polyethylene (PE) film was used as the film. No surface treatment was performed on the surface 11. On the other hand, as the surface treatment, the corona treatment was performed three times on the surface 12 using the batch-type corona treater.

At this time, the static water contact angle of the surface 11 was 96.7 degrees, and the contact angle hysteresis was 18.0 degrees. The static water contact angle of the surface 12 was 54.2 degrees, and the contact angle hysteresis was 50.3 degrees.

As the result, the membrane of the cell adhesion inhibitor formed on the surface 11 was largely transferred onto the surface 12. It is considered that, in this experiment, while the surface 11 remained hydrophobic, the surface 12 was strongly hydrophilized, and therefore, the membrane of the cell adhesion inhibitor formed on the surface 11 was transferred onto the surface 12, and was peeled off of the surface 11.

Comparative Example 13

The condition of the surface treatment was made different from that of Working Example 11, the other conditions were made similar to those of Working Example 11, and the experiment was performed.

Specifically, the polyethylene (PE) film was used as the film. As the surface treatment, the corona treatment was performed once on the surface 11 using the batch-type corona treater, and as the surface treatment, the corona treatment was performed three times on the surface 12 using the batch-type corona treater.

At this time, the static water contact angle of the surface 11 was 71.9 degrees, and the contact angle hysteresis was 43.6 degrees. The static water contact angle of the surface 12 was 54.2 degrees, and the contact angle hysteresis was 50.3 degrees.

As the result, the membrane of the cell adhesion inhibitor formed on the surface 11 was largely transferred onto the surface 12. It is considered that, in this experiment, the surface 12 was more strongly hydrophilized than the surface 11, and therefore, the membrane of the cell adhesion inhibitor formed on the surface 11 was transferred onto the surface 12, and was peeled off of the surface 11.

Comparative Example 14

The condition of the surface treatment was made different from that of Working Example 11, and the other conditions were made similar to those of Working Example 11, and the experiment was performed.

Specifically, the polyethylene (PE) film was used as the film. As the surface treatment, the corona treatment was performed three times on the surface 11 and the surface 12 using the batch-type corona treater.

At this time, the static water contact angles of the surface 11 and the surface 12 were 54.2 degrees, and the contact angle hystereses were 50.3 degrees.

As the result, the membrane of the cell adhesion inhibitor formed on the surface 11 was largely transferred onto the surface 12. It is considered that, in this experiment, both the surface 11 and the surface 12 were strongly hydrophilized similarly, and therefore, the membrane of the cell adhesion inhibitor formed on the surface 11 was transferred onto the surface 12, and was peeled off of the surface 11.

Thus, from the results of Comparative Examples 12 to 14, it was found that strongly hydrophilizing the surface 12 caused the cell adhesion inhibitor to be easily peeled off of the surface 11.

Working Example 13

The conditions of the film material and the surface treatment were made different from those of Working Example 11, the other conditions were made similar to those of Working Example 11, and the experiment was performed.

Specifically, the cyclic olefin copolymer (COC) film was used as the film. As the surface treatment, the corona treatment was performed three times on the surface 11 using the batch-type corona treater. No surface treatment was performed on the surface 12.

At this time, the static water contact angle of the surface 11 was 55.2 degrees, and the contact angle hysteresis was 48.8 degrees. The static water contact angle of the surface 12 was 97.0 degrees, and the contact angle hysteresis was 22.6 degrees.

As the result, the membrane of the cell adhesion inhibitor formed on the surface 11 was not transferred onto the surface 12. It is considered that, in this experiment, hydrophilizing the surface 11 improved the close contactness between the base material of the surface 11 and the cell adhesion inhibitor, while the surface 12 remained hydrophobic, and therefore, the cell adhesion inhibitor was not transferred from the surface 11 onto the surface 12, and was not peeled off.

Comparative Example 15

The condition of the surface treatment was made different from that of Working Example 13, the other conditions were made similar to those of Working Example 13, and the experiment was performed.

Specifically, the cyclic olefin copolymer (COC) film was used as the film. No surface treatment was performed on the surface 11 and the surface 12.

At this time, the static water contact angles of the surface 11 and the surface 12 were 97.0 degrees, and the contact angle hystereses were 22.6 degrees.

As the result, the membrane of the cell adhesion inhibitor formed on the surface 11 was slightly transferred onto the surface 12. It is considered that, in this experiment, both the surface 11 and the surface 12 remained hydrophobic, and therefore, the base material of the surface 11 and the cell adhesion inhibitor did not sufficiently adhere, and the cell adhesion inhibitor was transferred onto the surface 12 to be peeled off of the surface 11.

Working Example 14

The conditions of the kind of the cell adhesion inhibitor, its coating method, and the surface treatment were made different from those of Working Example 11, and the other conditions were made similar to those of Working Example 11, and the experiment was performed.

Specifically, the polyethylene (PE) film was used as the film. As the surface treatment, the corona treatment was performed three times on the surface 11 using the batch-type corona treater. No surface treatment was performed on the surface 12.

At this time, the static water contact angle of the surface 11 was 54.2 degrees, and the contact angle hysteresis was 50.3 degrees. The static water contact angle of the surface 12 was 96.7 degrees, and the contact angle hysteresis was 18.0 degrees.

As the cell adhesion inhibitor, polyvinyl alcohol (BIO-SURFINE (registered trademark)—AWP, Toyo Gosei Co., Ltd) that has an azido group in a side chain was used. After preparing this cell adhesion inhibitor into water solution of 1% and applying the cell adhesion inhibitor onto the surface 11 with the bar coater, the surface 11 was irradiated with a UV having a wavelength of 254 nm at a light amount of 0.7 J/cm$^2$ to be cured.

As the result, the membrane of the cell adhesion inhibitor formed on the surface 11 was not transferred onto the surface 12. It is considered that, in this experiment, hydrophilizing the surface 11 improved the close contactness between the base material of the surface 11 and the cell adhesion inhibitor, while the surface 12 remained hydrophobic, and therefore, the cell adhesion inhibitor was not transferred from the surface 11 onto the surface 12, and was not peeled off.

That is, even in the case where the kind of the cell adhesion inhibitor was made different, performing the hydrophilic treatment on the surface 11 ensured avoiding the transfer of the cell adhesion inhibitor from the surface 11 onto the surface 12.

Comparative Example 16

The condition of the surface treatment was made different from that of Working Example 14, the other conditions were made similar to those of Working Example 14, and the experiment was performed.

Specifically, the polyethylene (PE) film was used as the film. No surface treatment was performed on the surface 11 and the surface 12.

At this time, the static water contact angles of the surface 11 and the surface 12 were 96.7 degrees, and the contact angle hystereses were 18.0 degrees.

As the cell adhesion inhibitor, polyvinyl alcohol (BIO-SURFINE (registered trademark)—AWP, Toyo Gosei Co., Ltd) that has an azido group in a side chain was used. After preparing this cell adhesion inhibitor into water solution of 1% and applying the cell adhesion inhibitor on the surface 11 with the bar coater, the surface 11 was irradiated with a UV having a wavelength of 254 nm at a light amount of 0.7 J/cm$^2$ to be cured.

As the result, the membrane of the cell adhesion inhibitor formed on the surface 11 was slightly transferred onto the surface 12. It is considered that, in this experiment, both the surface 11 and the surface 12 remained hydrophobic, and therefore, the base material of the surface 11 and the cell adhesion inhibitor did not sufficiently adhere, and the cell adhesion inhibitor was transferred onto the surface 12 to be peeled off of the surface 11.

Working Example 15

After performing the surface treatment on a film with the same condition as that of Working Example 11, the static water contact angles and the contact angle hystereses of the surface 11 and the surface 12 were measured after a lapse of seven days at 50° C.

Specifically, the polyethylene (PE) film was used as the film. As the surface treatment, the corona treatment was performed once on the surface 11 using the batch-type corona treater. No surface treatment was performed on the surface 12.

After a lapse of seven days at 50° C., the static water contact angle of the surface 11 on which the corona treatment was performed once was 87.8 degrees, and the contact angle hysteresis was 43.9 degrees. The static water contact angle of the surface 12 on which no surface treatment was performed was 96.7 degrees, and the contact angle hysteresis was 18.0 degrees.

That is, as the result of storing the film on which the surface treatment was performed on the surface 11 for seven days at 50° C., it can be found that the static water contact angle of the surface 11 is recovered to a value indicating the hydrophobicity, which is close to a value without the surface treatment. In contrast to this, no large change was seen in the contact angle hysteresis of the surface 11 compared with Working Example 1.

Next, similar to Working Example 11, after applying the cell adhesion inhibitor to form the membrane on the surface 11, this membrane of the cell adhesion inhibitor was dyed with a coomassie blue and dried.

After the surface 12 was attached to this surface 11, and a load of 10 g/cm$^2$ was applied to be left to stand still for one minute, the surface 12 was peeled off of the surface 11.

As the result, the membrane of the cell adhesion inhibitor formed on the surface 11 was not transferred onto the surface 12.

That is, it is considered that, while the static water contact angle of the surface 11 was recovered to the value indicating the hydrophobicity, the contact angle hysteresis of the surface 11 presented a hydrophilized value, and thus, the close contactness between the base material of the surface 11 and the cell adhesion inhibitor improved, while the surface 12 remained hydrophobic, and therefore, the cell adhesion inhibitor was not transferred from the surface 11 onto the surface 12, and was not peeled off.

It has become apparent that, when while the static water contact angle of the surface 11 thus presents the value of hydrophobicity, the contact angle hysteresis of the surface 11 presents the hydrophilized value, it can be said that the surface 11 is hydrophilized, as described above.

Working Example 16

The condition of the surface treatment was made different from that of Working Example 15, the other conditions were made similar to those of Working Example 15, and the experiment was performed.

Specifically, the polyethylene (PE) film was used as the film. As the surface treatment, the corona treatment was performed three times on the surface 11 using the batch-type corona treater. No surface treatment was performed on the surface 12. After a lapse of seven days at 50° C., the static water contact angles and the contact angle hystereses of the surface 11 and the surface 12 were measured.

At this time, the static water contact angle of the surface 11 on which the corona treatment was performed three times was 85.3 degrees, and the contact angle hysteresis was 44.5 degrees. The static water contact angle of the surface 12 on which no surface treatment was performed was 96.7 degrees, and the contact angle hysteresis was 18.0 degrees.

That is, as the result of storing the film on which the surface treatment was performed on the surface 11 for seven days at 50° C., it can be found that the static water contact angle of the surface 11 is recovered to a value indicating the hydrophobicity, which is close to a value without the surface treatment. In contrast to this, no large change was seen in the contact angle hysteresis of the surface 11.

Next, similar to Working Example 11, after applying the cell adhesion inhibitor to form the membrane on the surface 11, this membrane of the cell adhesion inhibitor was dyed with a coomassie blue and dried.

After the surface 12 was attached to this surface 11, and a load of 10 g/cm² was applied to be left to stand still for one minute, the surface 12 was peeled off of the surface 11.

As the result, similar to Working Example 15, the membrane of the cell adhesion inhibitor formed on the surface 11 was not transferred onto the surface 12.

That is, it is considered that, while the static water contact angle of the surface 11 was recovered to the value indicating the hydrophobicity, the contact angle hysteresis of the surface 11 presented a hydrophilized value, and thus, the close contactness between the base material of the surface 11 and the cell adhesion inhibitor improved, while the surface 12 remained hydrophobic, and therefore, the cell adhesion inhibitor was not transferred from the surface 11 onto the surface 12, and was not peeled off.

Comparative Example 17

The condition of the surface treatment was made different from that of Working Example 15, the other conditions were made similar to those of Working Example 15, and the experiment was performed.

Specifically, the polyethylene (PE) film was used as the film. No surface treatment was performed on the surface 11 and the surface 12. After a lapse of seven days at 50° C., the static water contact angles and the contact angle hystereses of the surface 11 and the surface 12 were measured.

At this time, the static water contact angles of the surface 11 and the surface 12 were 96.7 degrees, and the contact angle hystereses were 18.0 degrees.

Next, similar to Working Example 11, after applying the cell adhesion inhibitor to form the membrane on the surface 11, this membrane of the cell adhesion inhibitor was dyed with a coomassie blue and dried.

After the surface 12 was attached to this surface 11, and a load of 10 g/cm² was applied to be left to stand still for one minute, the surface 12 was peeled off of the surface 11.

As the result, the membrane of the cell adhesion inhibitor formed on the surface 11 was transferred onto the surface 12. It is considered that, in this experiment, both the surface 11 and the surface 12 remained hydrophobic, and therefore, the base material of the surface 11 and the cell adhesion inhibitor did not sufficiently adhere, and the cell adhesion inhibitor was transferred onto the surface 12 to be peeled off of the surface 11.

Working Example 17

The condition of the surface treatment was made different from that of Working Example 11, the other conditions were made similar to those of Working Example 11, and the experiment was performed.

Specifically, the polyethylene (PE) film was used as the film. As the surface treatment, the excimer treatment was performed once on the surface 11 using the excimer irradiation apparatus (made by M. D. COM. Inc.). At this time, the conditions of the excimer treatment were 12 V, an irradiation distance of 4 mm, and a table moving speed of 5 mm/sec. No surface treatment was performed on the surface 12.

At this time, the static water contact angle of the surface 11 was 76.2 degrees, and the contact angle hysteresis was 41.8 degrees. The static water contact angle of the surface 12 was 96.7 degrees, and the contact angle hysteresis was 18.0 degrees.

As the result, the membrane of the cell adhesion inhibitor formed on the surface 11 was not transferred onto the surface 12. It is considered that, in this experiment, hydrophilizing the surface 11 improved the close contactness between the base material of the surface 11 and the cell adhesion inhibitor, while the surface 12 remained hydrophobic, and therefore, the cell adhesion inhibitor was not transferred from the surface 11 onto the surface 12, and was not peeled off.

That is, even in the case where the hydrophilic treatment method was made different from the corona treatment, performing the hydrophilic treatment on the surface 11 ensured avoiding the transfer of the cell adhesion inhibitor from the surface 11 onto the surface 12.

As described above, it has become apparent that hydrophilizing only the surface 11 or more strongly hydrophilizing the surface 11 than the surface 12 inside the culture container ensures relatively improving the close contactness between the base material of the surface 11 and the coating layer more than the close contactness between the base material of the surface 12 and the coating layer, and thus, the coating layer was not transferred from the surface 11 onto the surface 12, and the peeling was able to be avoided. On the other hand, it has become apparent that strongly hydrophilizing the surface 12 inside the culture container caused the coating layer to be easily peeled off of the surface 11.

It was found that, even in the case where the kind of the coating layer was made different, hydrophilizing only the surface 11 or more strongly hydrophilizing the surface 11 than the surface 12 inside the culture container ensures avoiding the transfer of the coating layer from the surface 11 onto the surface 12.

It is needless to say that one or more embodiments of the present invention are not limited to the above-described embodiments, and various kinds of changes can be made within a range of the one or more embodiments of the present invention.

For example, while in the above-described Working Examples, the polyethylene and the cyclic olefin copolymer were used as the base material of the culture container, another base material may be used as long as it is the polyolefin. As the surface treatment, it is not limited to the corona treatment or the excimer treatment as long as it presents hydrophilizing based on the value of the contact angle hysteresis, and another treatment can be used. Furthermore, it is possible to change as necessary, such as forming the membrane of the cell adhesion inhibitor on the upper surface and the lower surface inside the culture container.

One or more embodiments of the present invention can be appropriately used when iPS cells and the like are sphere cultured.

One or more embodiments of the present invention can be appropriately used for a packaging material and the like for manufacturing the cell culture container.

The entire contents of the documents described in the Description and Japanese Application as the basis of the priority claimed under the Paris Convention are hereby incorporated by reference.

DESCRIPTION OF REFERENCE SIGNS

1, 1a: Culture base material
11: First surface
12, 12a: Second surface
2: Coating layer Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A culture container made of a flexible packaging material, the culture container comprising:
a first side surface portion and a second side surface portion that are mutually opposed, wherein at least an inner surface side of the first side surface portion has a surface treatment such that, when a contact angle hysteresis is defined as a difference between an advance contact angle ($\theta a$) and a retreat contact angle ($\theta r$) at a time when water slips such that the contact angle hysteresis is equal to ($\theta a - \theta r$), a contact angle hysteresis of the surface on the inner surface side of the first side surface portion becomes larger than a contact angle hysteresis of a surface on an inner surface side of the second side surface portion, and a membrane made of a cell adhesion inhibitor is formed on the inner surface side of the first side surface portion,
wherein at least the inner surface side of the first side surface portion has a hydrophilic treatment,
wherein a base material of the inner surface side of the first side surface portion and a base material of the inner surface side of the second side surface portion consist of polyethylene, and
wherein the membrane made of a cell adhesion inhibitor is not formed on the inner surface side of the second side surface portion.

2. The culture container according to claim 1, wherein the cell adhesion inhibitor is at least any one of a phospholipid polymer or a polyvinyl alcohol derivative.

3. The culture container according to claim 1, wherein a plurality of wells are formed on the inner surface side of the first side surface portion.

* * * * *